(12) United States Patent
Jang et al.

(10) Patent No.: US 10,498,940 B2
(45) Date of Patent: Dec. 3, 2019

(54) ENDOSCOPE

(71) Applicant: Deuk Soo Jang, Seongnam-si, Gyeonggi-do (KR)

(72) Inventors: Deuk Soo Jang, Seongnam-si (KR); Chan Seob Jo, Daegu (KR)

(73) Assignee: Deuk Soo Jang, Seongnam-si, Gyeonggi-Do (KR)

( * ) Notice: Subject to any disclaimer, the term of this patent is extended or adjusted under 35 U.S.C. 154(b) by 260 days.

(21) Appl. No.: 15/141,956

(22) Filed: Apr. 29, 2016

(65) Prior Publication Data

US 2017/0311784 A1 Nov. 2, 2017

(51) Int. Cl.
| | | |
|---|---|---|
| *H04N 5/225* | (2006.01) | |
| *A61B 1/06* | (2006.01) | |
| *A61B 1/00* | (2006.01) | |
| *A61B 1/05* | (2006.01) | |

(52) U.S. Cl.
CPC ....... *H04N 5/2256* (2013.01); *A61B 1/00096* (2013.01); *A61B 1/00177* (2013.01); *A61B 1/051* (2013.01); *A61B 1/0615* (2013.01); *A61B 1/0684* (2013.01); *H04N 2005/2255* (2013.01)

(58) Field of Classification Search
CPC ............................... H04N 5/225; H04N 5/374
See application file for complete search history.

(56) References Cited

U.S. PATENT DOCUMENTS

| | | | | | |
|---|---|---|---|---|---|
| 4,467,361 | A | * | 8/1984 | Ohno ................... | G02B 23/243 250/208.1 |
| 5,368,036 | A | * | 11/1994 | Tanaka ..................... | A61B 8/12 600/104 |
| 5,835,142 | A | * | 11/1998 | Nakamura ........... | H04N 1/0311 348/335 |
| 6,211,904 | B1 | * | 4/2001 | Adair ................. | A61B 1/00082 257/E25.032 |
| 8,928,746 | B1 | * | 1/2015 | Stevrin .............. | G02B 23/2461 348/68 |
| 2006/0147492 | A1 | * | 7/2006 | Hunter ................... | A61B 17/11 424/426 |
| 2006/0195014 | A1 | * | 8/2006 | Seibel .................. | A61B 1/0008 600/102 |
| 2007/0213590 | A1 | * | 9/2007 | Squicciarini ....... | A61B 1/00087 600/172 |
| 2013/0085328 | A1 | * | 4/2013 | Kitano ............... | A61B 1/00096 600/110 |
| 2013/0317299 | A1 | * | 11/2013 | Fujii .................. | G02B 23/2438 600/176 |

FOREIGN PATENT DOCUMENTS

| | | | |
|---|---|---|---|
| JP | 62212613 | * | 9/1987 |
| JP | S6340117 A | | 2/1988 |
| JP | H10165419 A | | 6/1998 |

(Continued)

*Primary Examiner* — Md N Haque
(74) *Attorney, Agent, or Firm* — Novick, Kim & Lee, PLLC; Jae Youn Kim

(57) ABSTRACT

Provided is an endoscope, in which an image sensor is attached to a transducer probe such that the diameter of the transducer probe is reduced so as to decrease the feeling of irritation and prevent injuries of internal organs, and one or more light sources are attached to a leading end of the transducer probe so as to obtain images, which are clear and appropriate for purposes.

6 Claims, 3 Drawing Sheets

(56) References Cited

FOREIGN PATENT DOCUMENTS

Figure 1:
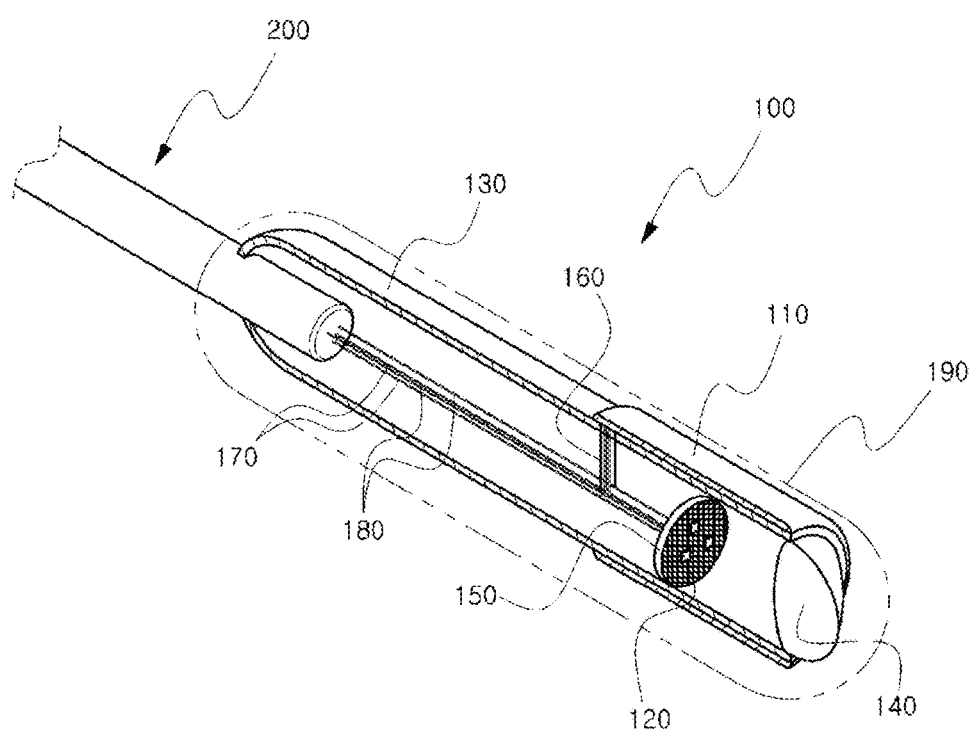

| | | | |
|---|---|---|---|
| JP | 2009189742 A | | 8/2009 |
| JP | 2013123628 A | | 6/2013 |
| JP | 2014-054499 A | | 3/2014 |
| KR | 10-2012-0101450 A | | 9/2012 |
| KR | 10-2014-0065231 A | | 5/2014 |
| KR | 1020160050576 | * | 10/2014 |

* cited by examiner

ENDOSCOPE

BACKGROUND OF THE INVENTION

Incorporation by Reference

Korean patent application No. 10-2014-0149041 filed in the Korean Intellectual Patent Office on Oct. 30, 2014, is hereby incorporated by reference in its entirety.

Field of the Invention

The present invention relates to an endoscope and, more particularly, to an endoscope, in which an image sensor is attached to the outer circumferential surface of a transducer probe and one or more light sources are attached to a leading end of the transducer probe such that the diameter of the transducer probe is reduced and thus searching can be carried out in the range of 360° in a very narrow space during an endoscopic examination as well as images, which are clear and appropriate for purposes, can be obtained.

Background Art

In general, endoscopes are illuminated optical devices such as subminiature periscopes, and typically divided into industrial endoscopes to be used for the examination of a pipe or a narrow space in ship-building and medical endoscopes to be used for the examination of an internal organ of a human body.

Particularly, the medical endoscope is an equipment to be directly inserted to the inside of a human body so as to visibly check and diagnose the inside of a human body by capturing images and is typically divided into an optical fiber endoscope and an electronic endoscope.

The optical fiber endoscope has two kinds of optical fibers, of which one serves as a light guide to light the inside of an organ of a patient and the other one serves as an image guide to transmit the image of a lesion from an objective lens at a leading end portion to human eyes, wherein since the light of external illumination is transmitted to the inside of a human body through the light guide, loss of light occurs in the process of the light transmission. Therefore, in order to secure sufficient illumination, the thickness of the light guide has to be increased. In addition, image signals are transmitted through the image guide so as to form images outside the human body. Therefore, the images are also likely to be lost or noise occurs during the transmission thereof such that it is difficult to secure high resolution and obtain accurate and detailed images.

To the contrary, the electronic endoscope has a sort of electronic camera such as a CCD or a CMOS, which is provided to the leading end thereof. Therefore, the electronic endoscope does not need any optical fiber as an image guide and only has optical fiber as a light guide for providing illumination. However, in order to secure sufficient illumination, the thickness of the optical fiber serving as a light guide has to be increased. In addition, due to the CCD or the CMOS provided to the leading end of the endoscope, the diameter of the endoscope is increased at the leading end portion such that the feeling of irritation becomes increased when the endoscope is inserted to the inside of a human body. Therefore, there is a problem that a patient complains of pain throughout an endoscopic examination.

Meanwhile, in order to solve the above-mentioned problems, there have been suggested a plurality of techniques with respect to an endoscope, for example, the disclosures of Korean Patent laid-open Publication No. 10-2014-0065231 and Korean Patent laid-open Publication No. 10-2012-0101450 and the like. However, all the endoscopes suggested in the prior art still have problems that, since an image sensor and a light source are all provided to the inside of the leading end of a cable, which is inserted to the inside of a human body, in a direction perpendicular to the axis of the cable and the light source has to be arranged so as to prevent the image sensor from interfering with light, the diameter of the endoscope is increased at the leading end portion and thus the feeling of irritation becomes increased when the endoscope is inserted to the inside of a human body. Therefore, there is still the problem that a patient complains of pain throughout an endoscopic examination.

Further, according to the prior art endoscopes, the image sensor captures the images of only forward portions in the advancing direction of the endoscope. Therefore, in order to check all the inside portions of an organ such as a small intestine, a large intestine, a stomach and the like, the endoscope has to be rotated or moved and the images obtained by the rotation or movement have to be edited to be combined with together by using additional image processing programs. Further, an examiner has to estimate the positions of corresponding images on the basis of the rotation or movement directions by memorizing positions which have been previously checked. Therefore, there is still a problem that it is difficult to provide an accurate diagnosis.

Meanwhile, the industrial endoscope, which is used in various industrial fields in the case where it is required to check the defects of a pipe-welding part or observe a narrow part, which people cannot approach, in the process of building a ship or manufacturing a machine and the like, has no particular difference from the medical endoscope in the configuration thereof, and also has the same technical problems as the medical endoscope, that is, the difficulty in obtaining accurate images due to the loss of light, the complicated manipulation and inaccurate diagnosis due to the fact that the inside of a human body cannot be observed through 360° at one view and the like except the problems relating to the injuries of a human body and infection occurred in the medical endoscope.

SUMMARY OF THE INVENTION

Accordingly, the present invention has been made to solve the above-mentioned problems occurring in the prior arts, and it is an objective of the present invention to achieve accurate examination and diagnosis by using an endoscope, in which an image sensor, which is conventionally positioned inside the leading end of a transducer probe, is attached to the outer circumference of a transducer probe such that the diameter of the transducer probe may be largely reduced, and the image sensor is attached in a shape, in which the image sensor encompasses all the outer circumference of the transducer probe, so as to realize simultaneous 360° observation such that, in the case of medical uses, the feeling of irritation as well as the injuries of an internal organ may be prevented during an endoscopic examination, thereby considerably reducing repulsion with respect to the endoscopic examination, and images of the insides of an organ such as a small intestine, a large intestine, stomach and the like may be obtained at a time. Further, in the case of industrial uses, the simultaneous 360° observation as well as a very narrow space observation may be also realized such that neither image edition nor position estimation are not required.

It is another objective of the present invention to achieve accurate examination and diagnosis by using the endoscope, in which the image sensor is not provided to the inside of the transducer probe as described above and a thus obtained space may be occupied by one or more light sources such that the loss of light does not occur and thus clear images can be obtained. Herein, if a plurality of light sources are provided, the lighting of the plurality of light sources may be controlled according to the use of the endoscope so as to obtain images as desired such that accurate examination and diagnosis may be realized through the endoscope.

It is a further objective of the present invention to form the endoscope in a disposable type so as to solve the problems of pollution and disease transmission in the case of medical uses.

To accomplish the above objectives, according to the present invention, there is provided an endoscope characterized in that an image sensor is provided to the outer circumferential surface of a housing, which forms a transducer probe, in close contact with the outer circumferential surface of the housing.

The housing includes a lens for diffusing light, which is provided to the leading end of the housing, and one or more light sources for irradiating light to the lens, which are provided to the rear side of the lens in the housing, wherein the light source includes red, green, blue, infrared and ultraviolet LEDs.

Further, the endoscope is formed in the shape of a capsule or in a cable-connecting type, and may be formed to be disposable.

According to the present invention structured as above, since the image sensor is provided in close contact with the outer circumferential surface of the housing, which forms the transducer probe of the endoscope, a margin may be provided to the internal space of the housing and the overall diameter of the transducer probe may be decreased such that the endoscope may be inserted into a very narrow space. Therefore, in the case of industrial uses, an accurate examination may be realized even for a very narrow space, which could not been previously examined, and, in the case of medical uses, the feeling of irritation is considerably reduced at the time of insertion and the injuries of internal organs may be minimized during an examination, such that a patient can receive an endoscopic examination comfortably.

Further, as described hereinabove, since the image sensor is attached in a shape, in which the image sensor encompasses the overall outer circumference of the transducer probe, the simultaneous 360° observation may be realized simply by moving the transducer probe forwards instead of rotating the endoscope in every direction, thereby simplifying the examination procedure. In addition, it is not necessary to estimate the positions where images are obtained and accordingly an accurate diagnosis may be realized.

Further, since the housing may have a margin provided to the internal space thereof as described above, one or more light sources may be provided to the corresponding space. Therefore, light may be directly irradiated and thus the loss of light may be decreased such that clear images may be obtained. In addition, compared to the prior art method of transmitting external light to the inside of a human body by using a light guide, according to the present invention, a plurality of light sources may be provided such that light may be irradiated as desired according to examination positions and purposes, thereby realizing an accurate diagnosis.

Further, if a special purpose light source for infrared rays or ultraviolet rays and the like is used as the light source, effects of treatment and the like may be also obtained.

Meanwhile, images are formed in the housing of the endoscope and image data is transmitted to the outside such that clear images may be obtained without loss or resistance occurred in the process of transmission.

BRIEF DESCRIPTION OF THE INVENTION

Figure 2:
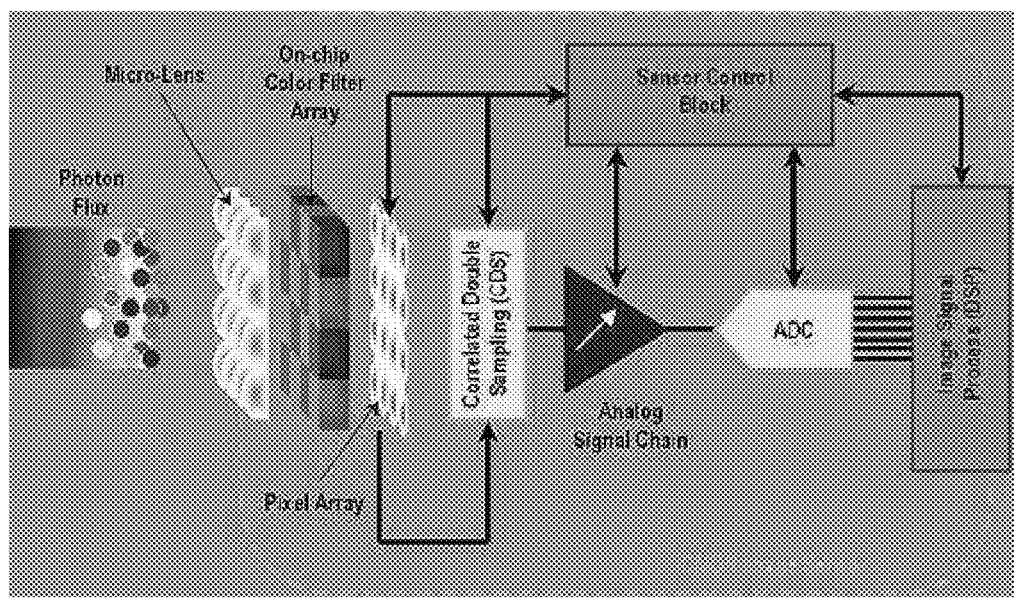
Figure 3:
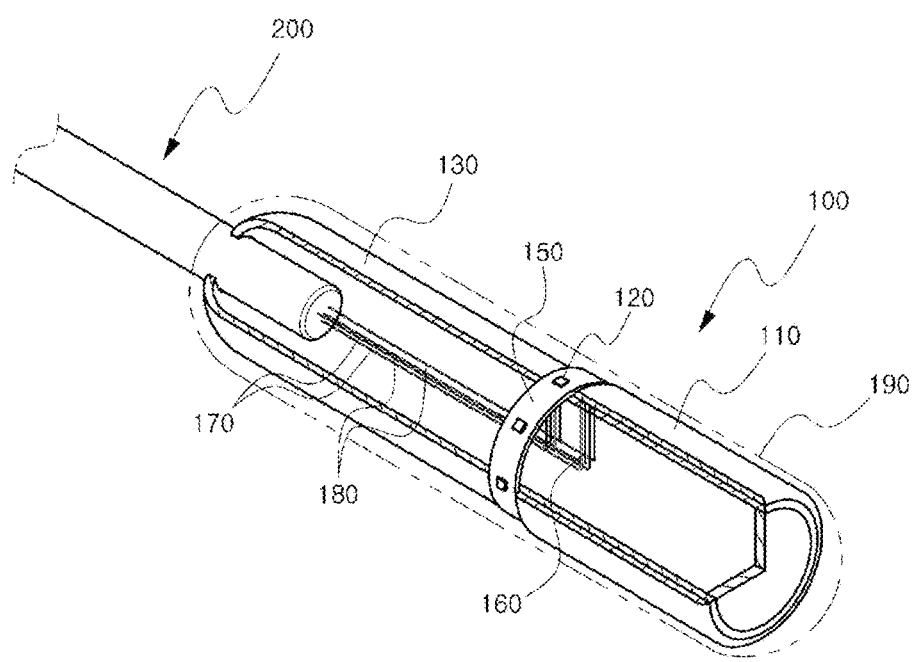

FIG. 1 is a partial cross-sectional view for showing the structure of an endoscope according to an embodiment of the present invention, FIG. 2 is a view for explaining the operation principles of a CMOS image sensor, and FIG. 3 is a view for showing an endoscope according to another embodiment of the present invention.

DETAILED DESCRIPTION OF THE PREFERRED EMBODIMENT

Reference will be now made in detail to the preferred embodiments of the present invention with reference to the accompanying drawings.

Referring to FIG. 1, an endoscope according to the present invention includes a transducer probe 100 having an image sensor 110 and a light source 120 and capturing images of the inside of a human body, and a cable 200 connected to the transducer probe 100 and transmitting or receiving signals. Hereinafter, for example, an endoscope for medical uses will be described with reference to a preferred embodiment of the present invention.

The transducer probe 100 includes a housing 130 formed in a shape, in which the housing 130 may minimize the feeling of irritation when the endoscope is inserted inside a human body, an image sensor 110 attached to the leading end of the housing 130 in close contact with the leading end of the housing 130, a lens 140 provided to the leading end of the housing 130 so as to be perpendicular to the central axis of the housing 130, and a light source 120 provided in the housing 130 at the rear portion of the lens 140.

In order to decrease the feeling of irritation, the housing 130 may be made from a plastic material into a cylindrical shape or a capsule shape and have additional grooves formed according to the attachment positions of the image sensors, which are not shown on the outer circumferential surface.

In addition, the image sensor 110 may be a well-known band-like image sensor, wherein, if the rear surface of the band-like image sensor becomes thin by grinding, the band-like image sensor is rolled backwards and thus easily adhered in a cylindrical shape to the outer circumferential surface of the housing 130 so as to be integrated with the housing 130. Herein, an adhesive agent such as epoxy resin and the like may be used.

Further, as for the image sensor 110, a plurality of image sensors may be arranged in a cylindrical shape and provided to the outer circumferential surface of the transducer probe.

As for the image sensor, it is possible to employ a CMOS image sensor. In addition, there has been developed a technique of realizing a CMOS circuit on a flexible substrate rather than a hard substrate. Therefore, it is possible to use a CMOS image sensor using such a flexible substrate. If such a flexible substrate is employed, the grinding of the rear surface of the image sensor may be omitted.

The complementary metal oxide semiconductor CMOS image sensor converts incident light into electric signals by each pixel so as to output the electric signals as digital data, differently from a CCD sensor. Herein, each pixel needs a circuit such that an area for receiving light is reduced. Therefore, the CMOS image sensor employs a micro-lens on each pixel, wherein the micro-lens focuses light on one position and amplifies the light such that each pixel can read an increased amount of light.

Considering the operations of the CMOS image sensor in more detail with reference to FIG. 2, first, as light passes through the micro-lenses (Micron Lens) and then a color filter array CFA, images are formed on the pixels and converted into electric signals so as to be completed as analogue image signals through correlated double sampling CDS and analogue processing, and the analogue image signals are outputted as digital signals through ADC. These are the normal operations of the CMOS image sensor.

Meanwhile, there is a recent tendency of using an integrated image sensor, in which the ADC output from the CMOS image sensor is received by a system on chip SOC such that image signal processing is carried out.

The lens 140 serves to diffuse the light irradiated from the light source 120, wherein a concave lens is used in the embodiment of the present invention.

The light source 120 employs one or more LEDs, wherein, for example, red, blue, green, infrared and ultraviolet LEDs may be used and any other kind of LEDs may be further used in accordance with circumstances.

The light source 120 is mounted on a substrate 150, which is provided to the inside of the housing 130, and the substrate 150 has a transmitting and receiving module (not shown) provided for transmitting or receiving data and connected to a power supply, wherein the substrate 150 is connected to the image sensor 110 through wire 160 bonding.

Further, even though the light source 120, which has three LEDs mounted on the substrate provided to the inside of the housing, has been particularly shown and described as an example with reference to FIG. 1, it is also possible to use a plurality of LEDs as shown in FIG. 3, wherein, similarly to the image sensor of FIG. 1, an accurate examination may be also carried out while reducing the diameter of the endoscope if the plurality of light sources 120 are attached to the outer circumferential surface of the housing 130. In this case, each one lens may be provided to the leading end of each of the light sources or it is also possible to use no lens.

In order to attach the light sources 120 to the outer circumferential surface of the housing, the technique of attaching the image sensor 120 is employed as it is such that the rear surface of the substrate provided with the plurality of LEDs may be formed thin by grinding, or a flexible circuit substrate may be used. Further, each of the plurality of LEDs may be mounted on the housing by bonding.

Meanwhile, a power line 170, which supplies power to the substrate, and a control line 180, which is formed of optical fiber and the like so as to transmit the data obtained by the image sensor to the outside and control signals for the light source and the like in the housing from an external controller to the transducer probe, are connected to the substrate 150 by penetrating the cable 200, wherein the cable is connected to the substrate by using a plug-shaped connector. In addition, even though both glass optical fiber and plastic optical fiber may be used as the optical fiber, it is more preferable to use the plastic glass fiber.

The endoscope described above is completed as an endoscope module by coating the outside portions of the housing and the cable at the leading end of the endoscope with transparent resin, for example, transparent silicon 190, which is not harmful to a human body. Thus finished endoscope may have a diameter of about 1 mm, since the size of one LED is to be about 0.2 mm×0.2 mm and the diameter of the image sensor is provided outside the housing. Further, if the five LEDs are all used, the endoscope may have a diameter of 2 mm or less since the five LEDs may be also provided to the outer circumferential surface of the housing in close contact with the outer circumferential surface of the housing, similarly to the image sensor.

As described above, the endoscope according to the present invention has a diameter of 2 mm or less such that the feeling of irritation is decreased when the endoscope is inserted to the inside of a human body and the injuries of internal organs in the human body may be prevented.

Further, according to the image sensor of the present invention, images are not formed outside but formed on the transducer probe and image data of thus formed images is transmitted to the outside through the optical fiber after compression or non-compression, such that clear images may be obtained without loss. Further, the image sensor is arranged in a cylindrical shape and obtains the images of the inside of an organ simultaneously into a ring shape while moving forward in the organ such that it is not necessary to rotate the transducer probe in several directions.

In addition, since the light source is provided to the transducer probe, no light guide is required but light is directly irradiated from the light source inside a human body such that bright images can be obtained without the loss of light. Also, it is possible to control the lighting of the light source by an external controller according to the position of a lesion or a purpose and thus carry out image analysis according to the luminance and color difference of images, thereby realizing an accurate diagnosis. If the infrared or ultraviolet rays are used in accordance with circumstances, treatment effects can be also obtained.

That is, if the light of the same color as the lesion to be examined is irradiated, the corresponding light is not absorbed into the lesion but reflected from the lesion such that an accurate image can be obtained. For example, it is effective to use red and infrared LEDs for cancer since the lesion of cancer has dark-red color. In addition, since a tumor and the like has white or yellow color, it is effective to use all of the red, green and blue LEDs so as to irradiate white light, or use the green and blue LEDs so as to irradiate yellow light. Further, since the height and the like of a lesion can be detected using the ultraviolet LED, the ultraviolet LED may be used for detecting the size of a corresponding tumor.

According to the present invention as described hereinabove, it is possible to obtain images with a high resolution of 8 mega-pixel or higher and largely reduce manufacturing costs by 1/10, compared to those of the prior art endoscopes. In addition, the endoscope may be manufactured as a disposable product, thereby solving the problems of pollution and disease transmission.

Meanwhile, even though the endoscope for medical uses has been particularly shown and described as an example hereinabove, the endoscope for industrial uses has the same mechanical configuration except the design for the prevention of human body injuries and infection and thus the detailed description thereof will be omitted.

Further, it is also possible to use a laser diode instead of the LEDs as the light source.

What is claimed is:
1. An endoscope, comprising a transducer probe including:
   a housing;
   an image sensor disposed on an outer circumferential surface of the housing;
   a light source mounted on a substrate disposed inside the housing; and a lens disposed at a leading end of the housing and configured to diffuse light irradiated from the light source, wherein an outside of the image sensor is coated with a transparent resin, and wherein the image sensor has a cylindrical shape covering the outer circumferential surface of the housing and is configured for simultaneous 360° observation of an organ.

2. The endoscope according to claim 1, wherein the light source is one of LED light sources including a red, a green, a blue, an infrared and an ultraviolet LEDs or combinations thereof, or a laser diode.

3. The endoscope according to claim 1, wherein the image sensor includes a hard substrate, wherein a thickness of the hard substrate is reduced by grinding a rear surface of the hard substrate, or a flexible substrate, and the image sensor is disposed in a close contact with the outer circumferential surface of the housing.

4. The endoscope according to claim 1, wherein the image sensor is integrally provided with the housing on the outer circumferential surface of the housing.

5. The endoscope according to claim 1, wherein the endoscope is for medical uses or for industrial uses.

6. An endoscope comprising a transducer probe including:

a housing;

an image sensor disposed on an outer circumferential surface of the housing; and a plurality of light sources disposed at a regular interval on a substrate having a cylindrical shape encompassing the outer circumferential surface of the housing as to be integrated with the outer circumferential surface of the housing, wherein an outside of the image sensor is coated with a transparent resin, and wherein the image sensor has a cylindrical shape covering the outer circumferential surface of the housing and is configured for simultaneous 360° observation of an organ.

* * * * *